United States Patent
Kannengiesser et al.

(10) Patent No.: US 10,083,505 B2
(45) Date of Patent: Sep. 25, 2018

(54) MAGNETIC RESONANCE APPARATUS AND METHOD FOR QUANTIFYING AN ORGAN FUNCTION

(71) Applicant: Siemens Healthcare GmbH, Erlangen (DE)

(72) Inventors: Stephan Kannengiesser, Wuppertal (DE); Berthold Kiefer, Erlangen (DE); Marcel Dominik Nickel, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/613,522

(22) Filed: Jun. 5, 2017

(65) Prior Publication Data

US 2017/0352156 A1  Dec. 7, 2017

(30) Foreign Application Priority Data

Jun. 6, 2016  (DE) .......... 10 2016 209 886

(51) Int. Cl.
| | |
|---|---|
| *G06K 9/00* | (2006.01) |
| *G06T 7/00* | (2017.01) |
| *G06T 7/136* | (2017.01) |
| *A61B 6/00* | (2006.01) |

(Continued)

(52) U.S. Cl.
CPC .......... *G06T 7/0012* (2013.01); *A61B 6/481* (2013.01); *G01R 33/34092* (2013.01); *G01R 33/4835* (2013.01); *G06T 7/0014* (2013.01); *G06T 7/0016* (2013.01); *G06T 7/136* (2017.01); *G06T 2207/10088* (2013.01); *G06T 2207/30056* (2013.01)

(58) Field of Classification Search
CPC .......... G06T 7/136; G06T 2207/30056; G06T 7/0014; G06T 7/0016; G06T 2207/10088; G06T 7/0012; A61B 6/481; G01R 33/34092; G01R 33/4835
USPC ........................................................ 382/131
See application file for complete search history.

(56) References Cited

U.S. PATENT DOCUMENTS

| | | | |
|---|---|---|---|
| 2010/0198054 A1* | 8/2010 | Ewing | A61B 5/055 600/420 |
| 2011/0098556 A1 | 4/2011 | Blomqvist et al. | |

(Continued)

OTHER PUBLICATIONS

Banerjee et al., "Multiparametric magnetic resonance for the non-invasive diagnosis of liver disease," EASL Journal of Hepatology, vol. 60, pp. 69-77 (2014).*

(Continued)

*Primary Examiner* — Gregory F Cunningham
(74) *Attorney, Agent, or Firm* — Schiff Hardin LLP (57) ABSTRACT

In a magnetic resonance method and apparatus for determination of a measurement variable that is relevant to a function of an organ of a patient, a first longitudinal relaxation rate $R_1^1$ is determined before a contrast medium is administered to the patient. A second longitudinal relaxation rate $R_1^2$ is determined after a contrast medium is administered to the patient. A property of the contrast medium in the organ is determined based on $R_1^1$ and $R_1^2$. The measurement variable is determined based on the property of the contrast medium in the organ.

11 Claims, 2 Drawing Sheets

(51) Int. Cl.
  *G01R 33/34* (2006.01)
  *G01R 33/483* (2006.01)

(56) References Cited

U.S. PATENT DOCUMENTS

2014/0330106 A1* 11/2014 Banerjee ............ G01R 33/4828
                                                      600/410
2015/0301141 A1* 10/2015 Griswold ........... G01R 33/5608
                                                      382/131
2016/0018434 A1    1/2016 Peppas

OTHER PUBLICATIONS

Ghugre et al., "Mechanisms of Tissue-Iron Relaxivity: Nuclear Magnetic Resonance Studies of Human Liver Biopsy Specimens," Magnetic Resonance in Medicine, vol. 54, pp. 1185-1193 (2005).*
Geisel et al., "Imaging-Based Liver Function Tests—Past, Present and Future," Leberfunktionstests—Fortschr. Rontgenstr., vol. 187, pp. 863-871 (2015).*
Bashir et al., "Hepatic MR imaging for in vivo differentiation of steatosis, iron deposition and combined storage disorder: Single-ratio in/opposed phase analysis vs. dual-ratio Dixon discrimination," European Journal of Radiology, vol. 81, pp. 101-109 (2012).*
Haimerl et al, "Volume-assisted estimation of liver function based on Gd-EOB-DTPA-enhanced MR relaxometry," Eur. Rad. (2015).*
Haimerl et al., "Volume-assisted estimation of liver function based on Gd-EOB-DTPA-enhanced MR relaxometry," Eur. Rad. (2015).
Geisel et al., "Imaging-Based Liver Function Tests—Past, Present and Future," Leberfunktionstests—Fortschr. Röntgenstr., vol. 187, pp. 863-871 (2015).

* cited by examiner

MAGNETIC RESONANCE APPARATUS AND METHOD FOR QUANTIFYING AN ORGAN FUNCTION

BACKGROUND OF THE INVENTION

Field of the Invention

The present invention concerns a method, a magnetic resonance apparatus, and also a non-transitory, computer-readable data storage medium for determining a measurement variable that is relevant to a function of an organ of a patient.

Description of the Prior Art

To determine a function of an organ, i.e. an organ function, blood examinations will frequently be carried out. For example the function of a liver can be obtained by blood tests before and after the injection of Indocyanine green (ICG). In this way a determination of the absolute liver function, a prediction of the post-operative liver function and/or a monitoring of the function increase after portal vein embolization can take place. ICG examinations are deemed to be the gold standard for determining the liver function.

In magnetic resonance imaging, the body of a person (patient) to be examined by a magnetic resonance scanner is usually subjected by a basic field magnet to a relatively high basic magnetic field, for example of 1.5 or 3 or 7 Tesla. In addition, gradient fields are activated by a gradient coil arrangement. Then radio-frequency pulses, for example excitation pulses, are radiated by a radio-frequency antenna unit by means of suitable antenna elements, which leads to the nuclear spin of specific atoms, which are resonantly excited by this radio-frequency pulse, being flipped by a defined flip angle in relation to the magnetic field lines of the basic magnetic field. During the relaxation of the nuclear spins, radio-frequency signals, called magnetic resonance signals, are emitted, which are received by suitable radio-frequency antennas and then further processed. Finally the desired image data can be reconstructed from the raw data acquired in this way.

Therefore, a specific magnetic resonance sequence is activated for a specific measurement, the sequence including a series of radio-frequency pulses, for example excitation pulses and refocusing pulses, as well as gradient switchings suitably coordinated thereto along different gradient axes in different spatial directions. Time-matched readout windows are activated, which specify the periods of time in which the induced magnetic resonance signals will be acquired.

The image data are spatially resolved and represent the reconstructed magnetic resonance signals. Depending on the magnetic resonance sequence used and also on the reconstruction method, the image data can have different contrasts and can reflect the anatomy or also specify different quantitative values.

In magnetic resonance imaging, depending on the clinical problem, a contrast medium may be administered to the patient. Contrast media, for example, can circulate in the blood stream or can attach to specific molecules or cells and can accumulate at those sites. At the places at which the contrast medium accumulates, the contrast medium changes the contrast of the image data and/or changes the quantitative values specified in the image data, compared to a recording without a contrast medium, in particular during use of an otherwise identical magnetic resonance sequence and reconstruction method. The accumulation of a contrast medium depends on the type of contrast medium. For example, contrast media are known that will be taken up and passed on by specific cell types. The concentration of such cell types accordingly is correlated with the concentration of the corresponding contrast medium. The concentration of a contrast medium is typically determined specifically for one contrast medium.

A clinical study (Haimerl et al., "Volume-assisted estimation of liver function based on Gd-EOB-DTPA—enhanced MR relaxometry", doi 10.1007/s00330-015-3919-5, Eur Radiol) has shown that magnetic resonance imaging using hepatocyte-specific contrast media, e.g. Primovist, Eovist, delivers comparable results to ICG examinations. In this case, the concentration of the hepatocyte-specific contrast medium correlates with the concentration of the healthy liver cells. The determination of the concentration of the hepatocyte-specific contrast medium is based on a measurement of the relaxation time $T_1$.

SUMMARY OF THE INVENTION

An object of the present invention is to provide a method for improved determination of a measurement variable that is relevant to a function of an organ of a patient by the operation of a magnetic resonance apparatus. A further object of the invention is to provide a magnetic resonance apparatus and a non-transitory, computer-readable data storage medium that are designed to implement such a method.

The inventive method for determining a measurement variable relevant to a function of an organ of a patient by operation of a magnetic resonance apparatus has the following steps. A first longitudinal relaxation rate $R_1^1$ of excited nuclear spins is determined in a processor from MR data acquired at a first contrast medium concentration. A second longitudinal relaxation rate $R_1^2$ of the excited nuclear spins is determined in the processor from MR data acquired at a second contrast medium concentration. A property of the contrast medium in the organ is determined in the processor based on $R_1^1$ and $R_1^2$. A measurement variable is determined in the processor based on the property of the contrast medium in the organ, and an electronic signal that represents the determined measurement variable is made available as an output from the processor.

The measurement variable to be determined in accordance with the inventive method is preferably characteristic for a function of an organ. The organ can be a prostate or a liver, for example. The function of the organ can be a function to be fulfilled for the patient by the organ. For example, the health of the organ can be a measure for the function of the organ. The measurement variable preferably quantifies a functionality of the organ. The measurement variable preferably specifies the health of the organ and/or indicates a disease. The measurement variable, for example, can specify the number of healthy and/or unhealthy cells of the organ. If the function of the organ is, for example, the creation of a flow of a liquid with a speed of flow, then the measurement variable can reflect the speed of flow. The measurement variable is preferably a variable representative for the function of the organ. A number of measurement variables can be determined for the organ. In such cases, the measurement variable can be specified in the form of a matrix, for example in the form of a spatial distribution, and/or as a scalar. The measurement variable can be an average value of at least two variables relevant to a function of an organ of the patient.

In magnetic resonance imaging, the longitudinal relaxation rate refers to the inverse longitudinal relaxation time $T_1$, which is also known as the spin-lattice relaxation time. For determining the first longitudinal relaxation rate, the scanner of the magnetic resonance apparatus will be activated at a first point in time, by a first magnetic resonance sequence, and first raw data are recorded. The first raw data are processed in accordance with a first reconstruction algorithm such that it identifies the first relaxation rate. For determining the second longitudinal relaxation rate, the magnetic resonance scanner is activated at a second point in time with the first magnetic resonance sequence, and second raw data are recorded. The second raw data are processed in accordance with the first reconstruction algorithm such that it identifies the second relaxation rate. The first and/or the second longitudinal relaxation rate can be specified, for example, in the form of a matrix and/or as a scalar. If the first and/or the second longitudinal relaxation rate are specified as a scalar, then the scalar is preferably the average value in the region covered by the organ.

The first longitudinal relaxation rate is preferably characteristic for the relaxation rate in the region covered by the organ at the first point in time of the application of the first magnetic resonance sequence. The second longitudinal relaxation rate is preferably characteristic for the relaxation rate in the region covered by the organ at the second point in time of the application of the first magnetic resonance sequence.

In this method, the medium to be administered to the patient will be referred to as a contrast medium, which can change a contrast and/or a quantitative value in the image data of the organ created by the first magnetic resonance sequence and with the first reconstruction algorithm and/or of a region of the patient affected as a result of the function of the organ. The contrast medium preferably changes the relaxation rate in the organ.

If the contrast medium is administered to a patient in a first quantity, then a first contrast medium concentration is present in the patient. A contrast medium concentration means the density of the contrast medium in the organ. For determining $R_1^1$, the first quantity of contrast medium has preferably already been administered. Preferably the first quantity is an empty quantity, so that the first contrast medium concentration is zero. Consequently, preferably no contrast medium has yet been administered to the patient at a first point in time within the framework of the examination. Consequently, the patient is preferably in a contrast-medium-free state at the first point in time. This means that no medium has been administered to the patient, and thus it is intentionally the case that no contrast medium is present in the organ at the first point in time. If a contrast medium has been administered at an earlier point in time than the first point in time, then, at the first point in time, the previously-administered contrast agent has preferably already been discharged from the patient. The determination of $R_1^1$ is preferably undertaken at the first point in time.

A second point in time is characterized by a second quantity of a contrast medium having been administered to the patient in advance. Based thereon, a second contrast medium concentration is present in the organ at the second point in time. The determination of $R_1^2$ is preferably undertaken at the second point in time. The contrast medium can also be administered at the second point in time. If, for example, Primovist or Eovist are administered as the contrast medium, then the second point in time preferably lies 20 minutes after the point in time of the administration of the contrast medium.

Based on $R_1^1$ and $R_1^2$, a property of the contrast medium will be determined. The property of the contrast medium preferably relates to the region of the organ and/or to a region of the patient affected as a result of the function of the organ. The property of the contrast medium can be, for example, a speed of flow of a medium transporting the contrast medium and/or the concentration of the contrast medium in a defined region. The defined region can be segmented for this purpose. The concentration preferably specifies the particle densities in the respective segments, and accordingly relates to the volume of each segment. The concentration can relate to the mass and/or the quantity of the substance.

The relaxation rates $R_1^1$ and $R_1^2$ are preferably present in the form of a quantity of data, which can be provided to a determination processor of the magnetic resonance apparatus via an input of the determination processor. Preferably a second algorithm is stored in the determination processor, which can be executed in the determination processor. This second algorithm preferably uses the quantity of data as an input parameter and calculates and/or determines the property of the contrast medium therefrom. The second algorithm is preferably designed so that the property will be determined in a manner that allows the property to be used in the further course of the method for a determination of the measurement variable, which is relevant to the function of the organ of the patient. The property of the contrast medium can be provided for such further processing as an output parameter via an output of the determination processor.

The relaxation rates $R_1^1$ and $R_1^2$ can depend on the concentration of the contrast medium. It has been recognized that for specific contrast media the relaxation rate is proportional to the concentration of the contrast medium. Consequently, the second algorithm can determine, from the difference between the relaxation rates $R_1^2-R_1^1$, the concentration of the contrast medium as a property of the contrast medium. For this purpose, the second algorithm can be provided with further information needed for carrying out the determination of the property of the contrast medium. The information is preferably provided to the determination processor for this purpose by the second algorithm accessing it and/or this information can be used as an input parameter. Based on the property of the contrast medium in the organ, the measurement variable can be determined. The determination is preferably undertaken by execution of a third algorithm in the determination processor.

An advantage of this method for determination of a measurement variable relevant for a function of an organ of a patient is that the method can be implemented by operation of an imaging apparatus. The method can be used instead of a biopsy and/or taking of blood in order to determine the function of the organ. Because of the large choice of contrast media and magnetic resonance sequences, the accuracy of the measurement variable determined can be better than that of a biopsy or taking of blood. With linear dependence of the difference of the relaxation rates $R_1^2-R_1^1$ on the concentration of the contrast medium as a property of the contrast medium, the concentration of the contrast medium can be determined especially accurately. The measurement variable to be determined from this concentration thus can also be specified especially accurately. The time required for the inventive method is preferably restricted to one doctor's appointment. The result of the examination is typically available immediately after the conclusion of the examination. The inventive determination of a function of an organ can be supplemented with little additional effort by image data, which show the anatomy and/or physiology of the organ. This enables diagnostic knowledge to be additionally enhanced.

In an embodiment of the method, the administered contrast medium is a hepatocyte-specific contrast medium. A hepatocyte-specific contrast medium typically contains a Gadolinium complex, which can be taken up by hepatocytes.

Typically only healthy and/or functional hepatocytes take up a Gadolinium complex. By taking up a Gadolinium complex, the signal strength of the hepatocytes can be increased in image data created by operation of a magnetic resonance scanner and/or the relaxation rate can be increased. Consequently the signal strength and/or the relaxation rate can correlate with the concentration of the contrast medium in the organ, i.e. in the region of the hepatocytes. This enables the number and/or concentration of the healthy and/or functional hepatocytes to be determined. Commercially-available examples of such a contrast medium are Primovist and Eovist. The advantage of using a hepatocyte-specific contrast medium lies in the fact that healthy and/or functional hepatocytes can be detected especially well, through which the function of an organ having hepatocytes can be determined and/or assessed especially well.

In another embodiment of the method, the organ is a liver. The function of the liver is an especially good indicator for oncological illness, which is why the assessment of its function is especially interesting. If the function of the liver is assessed in accordance with the inventive method, wherein a hepatocyte-specific contrast medium will preferably be employed, then, as a result of the linear dependency of the concentration of the contrast medium as a property of the contrast medium on the difference between the relaxation rates $R_1^2 - R_1^1$, a measurement variable relevant for a function of an organ of a patient can be determined especially accurately.

In another embodiment of the method, the measurement variable is a concentration of the healthy liver cells. Healthy liver cells are liver cells that fulfill a function allocated to them. The concentration of the healthy liver cells preferably specifies the volume density of the healthy liver cells. The concentration of the healthy liver cells can be the proportion of the healthy liver cells in all liver cells. The concentration of the healthy liver cells can be a relative concentration. Such a relative concentration can specify a ratio of the healthy liver cells to all liver cells. This form of embodiment is especially advantageous, since the function of the liver can be well characterized by the concentration of the healthy liver cells.

In another embodiment of the method, at least one parameter of the organ will be acquired and the at least one parameter will be taken into account in at least one of the following method steps of the inventive method:

The determination of a first longitudinal relaxation rate $R_1^1$ before an administration of a contrast medium to the patient, The determination of a second longitudinal relaxation rate $R_1^2$ after an administration of a contrast medium to the patient, The determination of a property of the contrast medium in the organ, based on and $R_1^2$, The determination of the measurement variable, based on the property of the contrast medium in the organ.

The parameter can be, for example, a variable specified by a magnetic resonance measurement for the organ. The parameter can be a variable that is known from a previous examination of the patient, for example a blood examination, and/or that is generally known for a patient and/or a specific illness and/or pathology.

The at least one parameter can be acquired by execution of a magnetic resonance measurement, and the at least one parameter can be present in the form of raw data and/or have been reconstructed into image data. Preferably the at least one parameter is present in the form of quantitative values. The acquisition of the at least one parameter can mean that the at least one parameter will be provided to the processor, for example in that it will be loaded into the processor. The acquisition of the at least one parameter can mean that the information will be loaded from a database. The at least one parameter can be stored in a memory, which is included in the magnetic resonance apparatus or is assigned to an external data medium or storage medium.

A parameter that can be taken into account in at least one method step of the inventive method, can be, for example, A proportion of fat, A concentration of a substance, such as iron for example, An elasticity, A transversal relaxation time $T_2$, A quantitative perfusion parameter, A diffusion coefficient.

The parameter preferably relates to the organ.

It is known from Ghugre et al., "Mechanisms of Tissue-Iron Relaxivity: Nuclear Magnetic Resonance Studies of Human Liver Biopsy Specimens", doi 10.1002/mrm.20697, MRM, that the relaxation time $T_1$ and thus the relaxation rates $R_1^1$ and $R_1^2$ depend on the concentration of iron in the liver. The change in the relaxation rates $R_1^1$ and $R_1^2$ because of iron typically falsifies the measurement variable determined in accordance with the inventive method, where the influence of iron on the relaxation rates $R_1^1$ and $R_1^2$ and/or on the determination of the relaxation rates $R_1^1$ and $R_1^2$ will not be taken into account. The concentration of iron typically correlates with the effective relaxation rate $R_2^*$, so that, based on a determination of $R_2^*$ in the organ by means of magnetic resonance imaging, the iron concentration in the organ can be established. Preferably, during the determination of the relaxation rates $R_1^1$ and $R_1^2$ the iron concentration will be taken into consideration such that the influence of the iron concentration on the relaxation rates $R_1^1$ and $R_1^2$ and/or on the method step of determining the relaxation rates $R_1^1$ and $R_1^2$ can be canceled out. A change of the relaxation rates $R_1^1$ and $R_1^2$ determined as a result of the presence of iron will be preferably be compensated for in accordance with this method. A multi-dimensional analysis, for example in the form of a cluster plot in accordance with Bashir et al., "Hepatic MR imaging for in vivo differentiation of steatosis, iron deposition and combined storage disorder: single-ratio in/opposed phase analysis vs. dual-ratio Dixon discrimination", doi 10.1016/j.ejrad.2011.01.067, Eur J Radiol, can be carried out for this. A corrected relaxation rate can also be computed, for example, in accordance with WO2013088149 A1.

An advantage of this embodiment of the method is that an influence of a parameter on the determination of the measurement variable can be compensated. This is advantageous when it is known that the parameters are negatively influencing the measurement variable, i.e. falsifying it. Taking into account this at least one parameter can increase the accuracy of the determination of the measurement variable.

In another embodiment of the method, $R_1^1$ and $R_1^2$ are determined such that these rates are spatially-resolved in a region encompassed by the organ, and the measurement variable will be determined so as to be spatially-resolved in the region encompassed by the organ. In the determination of $R_1^1$ and $R_1^2$, maps are preferably created, which specify the quantitative values as a function of spatial location. It is advantageous, particularly in the spatial region of the organ, for the relaxation rates to be represented in a spatially-distributed manner. Based on such $R_1^1$ and $R_1^2$ rates, the property of the concentration medium can likewise preferably be determined spatially-resolved as a function of the property. Based on this, a spatially-resolved measurement variable can be determined, which is relevant for the function of the organ. Such a measurement variable not only indicates a binary result, but also can provide information about the functioning of individual regions of the organ. This enables local changes of the organ to be verified and/or subregions of the organ to be identified, which contribute especially well or badly to the function of the organ. Such a measurement variable can represent, for example, a disease of the organ, and/or the progress of the disease, especially well. Likewise a therapeutic treatment can be monitored dependent on the variable or surgical interventions can be planned. In comparison with determining the function of a liver by an ICG test, the function of a liver can be determined in accordance with this method in an especially detailed and accurate manner.

In another embodiment of the method, the organ is segmented into at least two segments encompassed by the organ and, during determination of the measurement variable, a segmented measurement variable is determined for each of the at least two segments. $R_1^1$ and $R_1^2$ and/or the measurement variable are preferably determined spatially-resolved. Based thereon and/or on further image data, which have been recorded in a magnetic resonance examination of the organ, a segmentation of the organ, i.e. a delimitation of the organ from its environment, can take place and/or a segmentation of the organ into at least two segments, i.e. into at least two subregions of the organ, can be implemented. The segments are preferably selected so that, within a segment, $R_1^1$ and/or $R_1^2$ and/or the measurement variable and/or the property of the contrast medium are more similar to one another than $R_1^1$ and/or $R_1^2$ and/or the measurement variable and/or the property of the contrast medium in the at least one other segment. Based on the spatially-resolved measurement variable, a segmented measurement variable can be specified for each segment, which is relevant for the function of the organ in this segment. The segmented measurement variable is preferably a scalar, for example an average value. The advantage of this embodiment is that the function of the liver can be separately quantified in individual segments, i.e. sub-areas or regions.

In another embodiment of the method, a volume of the organ is determined and, based on the volume and the measurement variable, a value for the function of the organ is determined. In a further method step, the volume of the organ can be determined. This can be done, for example, based on a segmentation of the organ, i.e. a delimitation of the organ from its environment. If, for example, the concentration of the contrast medium and/or the concentration of the healthy liver cells are known as the measurement variable, then with knowledge of the volume, the absolute number of healthy liver cells can be established. Such an absolute number is suitable, for example, for comparing the organ of the patient with organs of other patients and/or for observing a change to an organ of a patient over time.

The inventive magnetic resonance apparatus has a computer with a determination processor, which is designed for carrying out the inventive method as described above for determination of a measurement variable that is relevant for a function of an organ of a patient. Thus the inventive magnetic resonance apparatus is designed to implement the inventive method with the determination processor. For this purpose, the determination processor has an input and an output. Data, for example raw data recorded by the scanner of the magnetic resonance apparatus, which are needed for determining the first and/or the second longitudinal relaxation rate $R_1^1$ and/or $R_1^2$ in the organ, are provided to the determination processor via the input thereof. Further functions, algorithms or parameters needed in the method can be provided to the determination processor via the input. The determination processor is configured to determine a first and/or second longitudinal relaxation rate $R_1^1$ and/or $R_1^2$ and/or to determine a property of the contrast medium in the organ based on $R_1^1$ and $R_1^2$ and/or the measurement variable based on the property of the contrast medium in the organ. The relaxation rates and/or properties and/or measurement variables determined are provided via the output. The determination processor can be integrated into the magnetic resonance apparatus. The determination processor also can be installed separately from the magnetic resonance apparatus. The determination processor can be connected to the magnetic resonance apparatus.

Embodiments of the inventive magnetic resonance apparatus correspond to embodiments of the inventive method as described above. The magnetic resonance apparatus can have further controller components, which are needed and/or advantageous for carrying out the inventive method. The magnetic resonance apparatus can also be designed to send control signals and/or to receive control signals and/or to process such signals, in order to carry out the inventive method. Preferably, the determination processor is part of the computer of the inventive magnetic resonance apparatus. Computer programs and further software can be stored on a memory of the computer, with which the determination processor automatically controls and/or executes the inventive method.

The determination processor of the magnetic resonance apparatus preferably has a neural network that operates according to a self-learning algorithm, which is designed to carry out the inventive method independently. The relaxation rates, measurement variables, properties of the contrast medium and where necessary further measurement variables specified during an execution of the inventive method can be stored in a memory of the magnetic resonance apparatus as data. The self-learning algorithm preferably analyzes the data automatically. To do this the self-learning algorithm can be designed to analyze the data in the form of multi-parametric distributions and/or for example, by machine learning, delivers results in the form of binary decisions, evaluations or in the form of multiple values. The self-learning algorithm can also be designed to find multi-dimensional decision boundaries that do not correspond to simple hyper levels in the multi-parametric space.

The present invention also encompasses a non-transitory, computer-readable data storage medium encoded with programming instructions that is loadable into a control computer of a magnetic resonance apparatus. The program code causes the control computer to operate the magnetic resonance apparatus in order to implement the embedded method as described above, when the program code is executed by the control computer.

Examples of electronically-readable data media are a DVD, a magnetic tape or a USB stick, on which electronically-readable control information, in particular software, is stored.

The advantages of the inventive magnetic resonance apparatus and the inventive non-transitory, computer-readable data storage medium essentially correspond to the advantages of the inventive method described above in detail. Features, advantages and embodiments described for the method are applicable to the other aspects of the invention.

DESCRIPTION OF THE PREFERRED EMBODIMENTS

Figure 1:
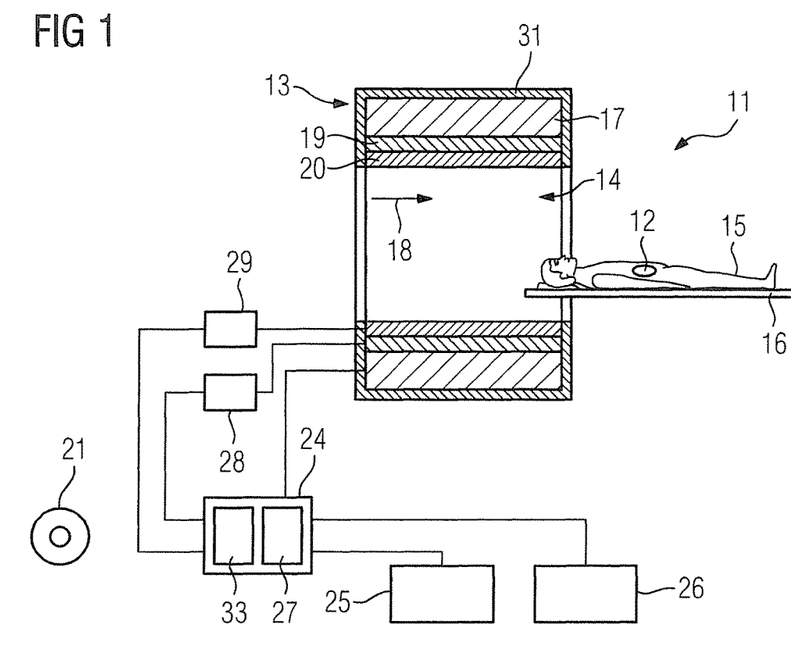
FIG. 1 shows an inventive magnetic resonance device in a schematic illustration.

FIG. 1 schematically illustrates an inventive magnetic resonance apparatus 11 for carrying out the inventive method. The magnetic resonance apparatus 11 has a scanner 13 with a basic field magnet 17 that generates a strong and constant basic magnetic field 18. The scanner 13 has a cylindrical patient receiving area 14 for receiving a patient 15. The patient receiving area 14 is circumferentially surrounded by the scanner 13. The patient 15 has an organ 12 and can be moved by a patient support 16 into the patient receiving area 14. The patient support 16 has a patient table that is movable within the scanner 13. The scanner 13 is screened from the outside by a housing 31.

The scanner 13 furthermore has a gradient coil arrangement 19, for spatially encoding the magnetic resonance signals. The gradient coil arrangement 19 is activated by a gradient controller 28. Furthermore the scanner 13 has a radio-frequency antenna 20, which in this embodiment is a body coil permanently integrated into the scanner 13, and a radio-frequency antenna controller 29. The radio-frequency antenna 20 is activated by the radio-frequency antenna controller 29 so as to radiate radio-frequency pulses into an examination space, which is essentially formed by the patient receiving area 14. The radiation radio-frequency pulses give certain nuclear spins in the patient 15 a magnetization that deflects those nuclear spins from the direction of the basic magnetic field 18 by a defined angle, called a flip angle. As the excited nuclear spins relax and thereby return to the steady state, they emit radio-frequency signals, which are the aforementioned magnetic resonance signals. These magnetic resonance signals may be detected by the same antenna that was used to radiate the radio-frequency pulses, or may be detected by a different antenna in the scanner 13.

For control of the basic field magnet 17, the gradient controller 28 and the radio-frequency antenna controller 29, the magnetic resonance apparatus 11 has a computer 24.

The computer 24 centrally controls the magnetic resonance apparatus 11, such as to execute MR control sequences. Control information such as imaging parameters, as well as reconstructed image data, can be displayed to the user on a display 25, for example on at least one monitor. In addition, the magnetic resonance apparatus 11 has an input unit 26, via which information and/or imaging parameters can be entered by a user during a measurement process. The computer 24 can include the gradient controller 28 and/or the radio-frequency antenna controller 29 and/or the display 25 and/or the input unit 26. The computer 24 further has a determination processor 33. The magnetic resonance apparatus 11 is thus designed, together with the determination processor 33, to implement the inventive method. The computer 24 preferably has a neural network 27 with a self-learning algorithm, which is designed to carry out the inventive method independently.

The magnetic resonance apparatus 11 shown can of course include further components, common to magnetic resonance apparatuses. The general manner in which a magnetic resonance apparatus functions is known to those skilled in the art, so that a more detailed description is not necessary herein.

The method described herein can also be available in the form of a computer program product, which implements the respective method on the computer 24, when it is executed by the computer 24. A non-transitory, computer-readable data storage medium 21 with electronically-readable control information stored thereon is designed such that, when the data storage medium 21 is loaded into the computer 24, the control information cause the computer 24 to execute the described method.

Figure 2:
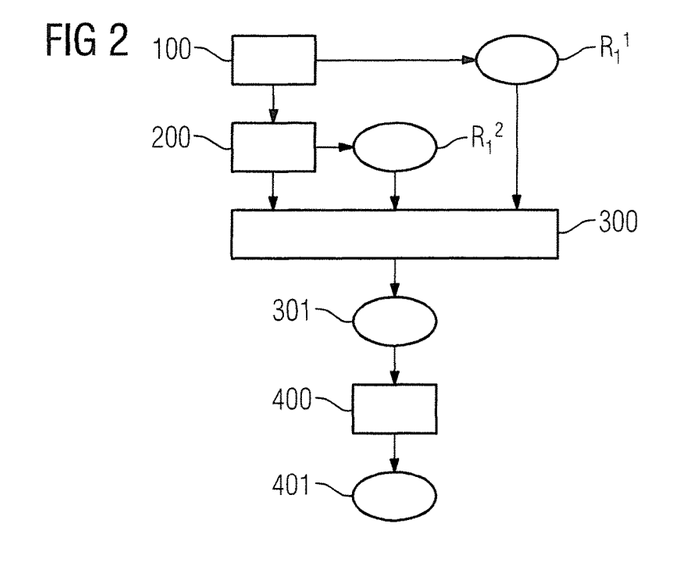
FIG. 2 is a flowchart of a first embodiment of the inventive method.

FIG. 2 is a flowchart of a first embodiment of an inventive method for a determination of a measurement variable 401 relevant for a function of an organ 12 of a patient 15 by operating the magnetic resonance apparatus 11. In this case, the method proceeds in accordance with the following method steps.

In method step 100 a first longitudinal relaxation rate $R_1^1$ will be determined at a first contrast medium concentration. At a second contrast medium concentration a second longitudinal relaxation rate $R_1^2$ will be determined in method step 200. $R_1^1$ and $R_1^2$ will preferably be determined such that these rates are present spatially-resolved in a region covered by the organ 12. Based on $R_1^1$ and $R_1^2$, in method step 300, a property of the contrast medium 301 in the organ 12 will be determined. Based on the property of the contrast medium 301 in the organ 12, in method step 400 the measurement variable 401 will be determined. If $R_1^1$ and $R_1^2$ are present spatially-resolved, the measurement variable 401 will preferably be determined such that this is present spatially-resolved in the region covered by the organ 12. The organ 12 is preferably a liver. The administered contrast medium is preferably a hepatocyte-specific contrast medium. The measurement variable 401 is preferably a concentration of the healthy liver cells.

Figure 3:
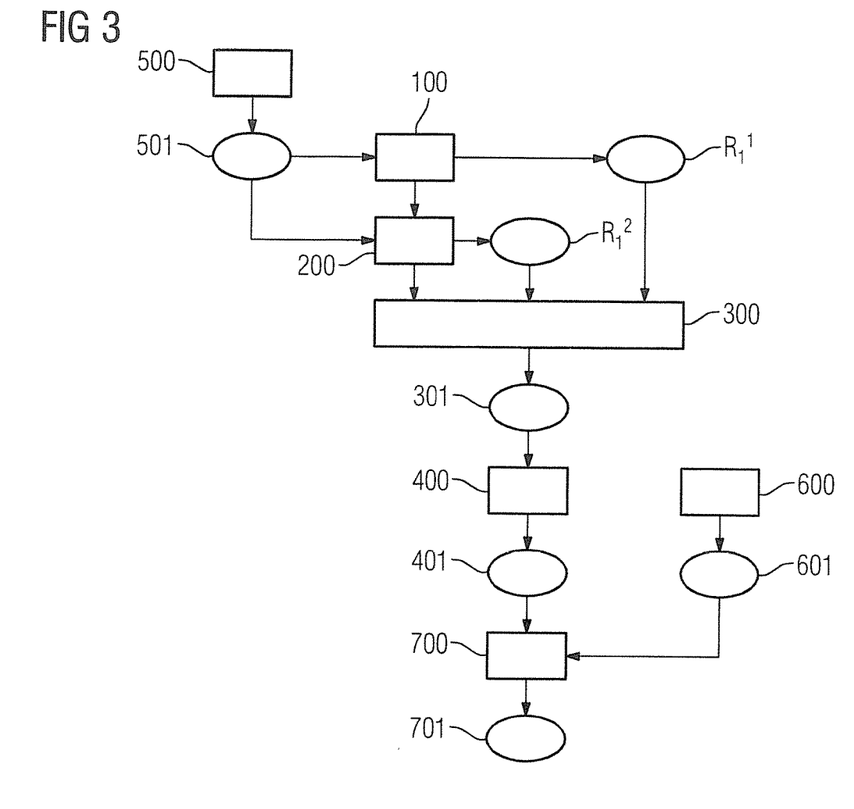
FIG. 3 is a flowchart of a second embodiment of the inventive method.

FIG. 3 is a flowchart of a second embodiment of the inventive method. The flow diagram of the second form of embodiment is based on the flowchart of the first embodiment and supplements that flowchart by further method steps. These further method steps are optional.

Before the determination of the first longitudinal relaxation rate $R_1^1$ in accordance with method step 100, a parameter 501 of the organ 12 is preferably available to the method, which was preferably acquired at the beginning of the method in method step 500. The acquired parameter 501 will preferably be taken into account in the determination of $R_1^1$ and/or $R_1^2$ in the method steps 100 and/or 300. Method step 500 can also be integrated into method step 100 or at least be partly executed at the same time. The parameter 501 typically influences $R_1^1$ and/or $R_1^2$ and/or their determination, so that deviations of $R_1^1$ and/or $R_1^2$ are produced as a result of the parameter 501. These deviations are preferably compensated in the determination of $R_1^1$ and/or $R_1^2$ in the method steps 100 and/or 300.

Furthermore, in method step 600, a volume 601 of the organ 12 can be determined. This can be done, for example, based on magnetic resonance imaging data, wherein the organ 12 will be segmented. Taking account of the volume 601 and the measurement variable 401, in method step 700, a value 701 for the function of the organ 12 can be determined. The value is preferably an absolute value, which quantifies the function of the organ 12 and can be employed for example for a comparison of the organ function between different patients. The parameter 501 can also be taken into account in the method steps 400 and/or 600 and/or 700.

Figure 4:
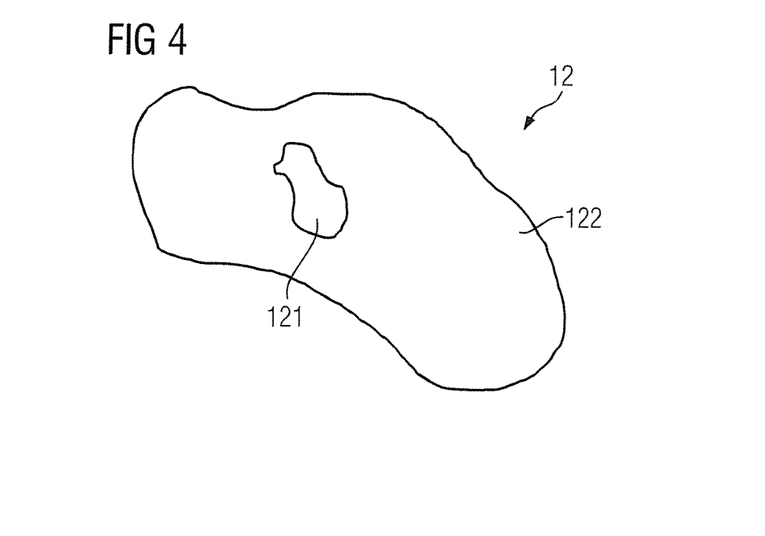
FIG. 4 schematically illustrates a segmented organ.

FIG. 4 schematically illustrates a segmented organ 12 with a first segment 121 and a second segment 122. Within the framework of the inventive method, in an independent method step, a segmentation of the organ 12 into at least two segments 121, 122 covered by the organ can take place and on determination of the measurement variable 401, for each of the at least two segments 121, 122, a segmented measurement variable can be determined. The first segment 121 and the second segment 122 are preferably disjoint from one another. The segmentation can be done for example on the basis of a spatially-resolved $R_1^1$ and/or $R_1^2$, so that for example the second segment 122 differs from the first segment 121 in $R_1^1$ and/or $R_1^2$. The union of sets of the two segments 121, 122 preferably produces the volume 601 of the organ 12.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for determining a measurement variable relevant to a function of an organ of a patient, by operation of a magnetic resonance (MR) apparatus, said method comprising:
    operating an MR data acquisition scanner, while a patient is situated therein, to acquire first MR data representing a first longitudinal relaxation rate $R_1^1$ of nuclear spins in an organ of the patient at a first contrast medium concentration;
    operating the MR data acquisition scanner while the patient is situated therein to acquire second MR data representing a second longitudinal relaxation rate $R_1^2$ of the nuclear spins of the organ at a second contrast medium concentration;
    providing said first and second MR data to a processor and, in said processor, determining a property of the contrast medium in the organ based on $R_1^1$ and $R_1^2$;
    in said processor, determining a measurement variable that is relevant to a function of the organ based on said property of the contrast medium in the organ; and
    making a non-transitory electronic signal representing said measurement variable available from the processor as an output.

2. A method as claimed in claim 1 comprising using a hepatocyte-specific contrast medium as said contrast medium.

3. A method as claimed in claim 1 wherein the organ is the liver of the patient.

4. A method as claimed in claim 3 wherein said measurement variable is a concentration of healthy liver cells.

5. A method as claimed in claim 1 comprising also acquiring at least one parameter of the organ and using said at least one parameter in said processor to make at least one determination selected from the group consisting of a determination of $R_1^1$ before administering the contrast medium to the patient, determining $R_1^2$ after the contrast medium is administered to the patient, determining the property of the contrast medium in the organ based on $R_1^1$ and $R_1^2$, and determining said measurement variable based on said property.

6. A method as claimed in claim 1 comprising determining each of $R_1^1$ and $R_1^2$ in a spatially-resolved manner in a region encompassed by said organ, and determining said measurement variable also in a spatially-resolved manner in said region.

7. A method as claimed in claim 6 comprising segmenting the organ into at least two segments of the organ, and determining said measurement variable in each of said at least two segments.

8. A method as claimed in claim 1 comprising, in said processor, determining a volume of the organ and, based on said volume and said measurement variable, determining a value that is also relevant to the function of the organ.

9. A magnetic resonance (MR) apparatus comprising:
    an MR data acquisition scanner;
    a control computer configured to operate said MR data acquisition scanner, while a patient is situated therein, to acquire first MR data representing a first longitudinal relaxation rate $R_1^1$ of nuclear spins in an organ of the patient at a first contrast medium concentration;
    said control computer being configured to operate the MR data acquisition scanner while the patient is situated therein to acquire second MR data representing a second longitudinal relaxation rate $R_1^2$ of the nuclear spins of the organ at a second contrast medium concentration;
    a processor provided with said first and second MR data, said processor being configured to determine a property of the contrast medium in the organ based on $R_1^1$ and $R_1^2$;
    said processor being configured to determine a measurement variable that is relevant to a function of the organ based on said property of the contrast medium in the organ; and
    said processor being configured to make a non-transitory electronic signal representing said measurement variable available from the processor as an output.

10. A computer for determining a measurement variable relevant to a function of an organ of a patient, by operation of a magnetic resonance (MR) apparatus, said method comprising:
    an input interface that receives first MR data, acquired from an MR data acquisition scanner while a patient is situated therein, representing a first longitudinal relaxation rate $R_1^1$ of nuclear spins in an organ of the patient at a first contrast medium concentration;
    said input interface also receiving second MR data representing a second longitudinal relaxation rate $R_1^2$ of the nuclear spins of the organ, acquired from said MR data acquisition scanner while the patient is situated therein, at a second contrast medium concentration;
    a processor configured to determine a property of the contrast medium in the organ based on $R_1^1$ and $R_1^2$;
    said processor being configured to determine a measurement variable that is relevant to a function of the organ based on said property of the contrast medium in the organ; and
    an output interface at which said processor is configured to make a non-transitory electronic signal representing said measurement variable available from the processor as an output.

11. A non-transitory, computer-readable data storage medium encoded with programming instructions, said storage medium being loaded into a computer of a magnetic resonance (MR) apparatus that comprises an MR data acquisition scanner, said programming instructions causing said computer to:
    receive first MR data, acquired from an MR data acquisition scanner while a patient is situated therein, representing a first longitudinal relaxation rate $R_1^1$ of nuclear spins in an organ of the patient at a first contrast medium concentration;
    receive second MR data, acquired from said MR data acquisition scanner while the patient is situated therein, representing a second longitudinal relaxation rate $R_1^2$ of the nuclear spins of the organ at a second contrast medium concentration;

determine a property of the contrast medium in the organ based on $R_1^1$ and $R_1^2$;

determine a measurement variable that is relevant to a function of the organ based on said property of the contrast medium in the organ; and make a non-transitory electronic signal representing said measurement variable available from the computer as an output.

* * * * *